(12) United States Patent
Tanaka et al.

(10) Patent No.: US 6,906,197 B2
(45) Date of Patent: Jun. 14, 2005

(54) PROCESS FOR THE PREPARATION OF OPTICALLY ACTIVE AMINES OR SALTS THEREOF

(75) Inventors: Hiroki Tanaka, Arai (JP); Li Rui Pan, Arai (JP); Kiyoshi Ikura, Arai (JP)

(73) Assignee: Daicel Chemical Industries, Ltd, Osaka (JP)

(*) Notice: Subject to any disclaimer, the term of this patent is extended or adjusted under 35 U.S.C. 154(b) by 151 days.

(21) Appl. No.: 10/310,805

(22) Filed: Dec. 6, 2002

(65) Prior Publication Data

US 2003/0139628 A1 Jul. 24, 2003

(30) Foreign Application Priority Data

Dec. 6, 2001 (JP) ........................................ 2001-373243

(51) Int. Cl.$^7$ .......................................... C07D 209/54
(52) U.S. Cl. ...................................................... 548/408
(58) Field of Search ........................................ 548/408

(56) References Cited

FOREIGN PATENT DOCUMENTS

| EP | 0 357 047 A1 | 3/1990 |
|----|---|---|
| EP | 0 829 473 A1 | 3/1998 |
| JP | 11-240867 A | 9/1999 |
| JP | 11-240868 A | 9/1999 |

OTHER PUBLICATIONS

STN International ® CAPLUS Database, Accession No. 1995:987954; Kanbara et al., JP 07224033, abstract.*
Jan Jorn Hansen et al.; Acta Chemica Scandinavica; Series B; vol. 28; No. 4; 1974; pp. 418–424; XP001109799.
Hiroyuki Nohira et al., Bulletin of the Chemical Society of Japan; vol. 43; No. 7; 1970; pp. 2230–2233; XP001109796.
Gerrit Limberg et al.; SYNTHESIS; No. 1; 1999; pp. 178–183; XP0001091282.
B. Minder et al.; Journal of Catalysis; vol. 160; 1996; pp. 261–268; XP0001091313.
Yuji Minoura et al.; J. Am. Chem. Soc.; vol. 81; 1959; pp. 4689–4692; XP002258890.
Arie Gutman, et al.; Tetrahedron: Asymmetry; vol. 9, No. 24; Dec. 24, 1998; pp. 4369–4379; XP004150938.
Wolfgang Wiehl et al.; Chem. Ber.; vol. 119; 1986; pp. 2668–2677; XP002248465.
Lie Kyo Liem et al.; Arch. Pharm. (Weinheim); vol. 324; 1991; pp. 335–347; XP001091223.
David Nichols et al.; J. Med. Chem.; vol. 31, No. 7; 1988; pp. 1406–1412; XP001149357.
James Marshall et al.; J. Am. Chem. Soc.; vol. 110; 1988; pp. 2925–2931; XP002248466.

* cited by examiner

*Primary Examiner*—Ceila Chang
*Assistant Examiner*—Sonya Wright
(74) *Attorney, Agent, or Firm*—Birch, Stewart, Kolasch & Birch, LLP

(57) ABSTRACT

A process produces an optically active amine or its salt and includes the steps of reacting a ketone of Formula (1a)

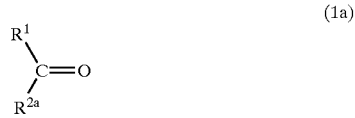

(1a)

wherein $R^1$ is typically an unsubstituted or substituted hydrocarbon group; and $R^{2a}$ is typically a hydrocarbon group having at least one oxo group and optionally having other substituent, with an optically active amine of Formula (2):

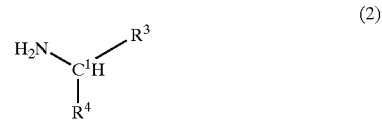

(2)

wherein $R^3$ is an unsubstituted or substituted aryl group; $R^4$ is an unsubstituted or substituted lower alkyl group; and $C^1$ is an asymmetric carbon atom, in the presence of an organic acid to thereby yield a corresponding optically active imine, hydrogenating the imine in the presence of a catalyst to yield a corresponding amine, subjecting the amine or its salt to hydrogenolysis in the presence of a catalyst, and reducing the hydrogenolyzed product with a reducing agent.

5 Claims, No Drawings

US 6,906,197 B2

PROCESS FOR THE PREPARATION OF OPTICALLY ACTIVE AMINES OR SALTS THEREOF

This nonprovisional application claims priority under 35 U.S.C. §119(a) on patent application Ser. No. 2001-373243 filed in Japan on Dec. 6, 2001, which is herein incorporated by reference.

BACKGROUND OF THE INVENTION

1. Field of the Invention

The present invention relates to processes for the preparation of optically active amines or salts thereof and processes for the preparation of optically active imines. The invention also relates to novel optically active amines and salts thereof and to novel optically active imines.

2. Description of the Related Art

Certain optically active amines are known in the art as intermediates for medical drugs and agricultural chemicals. For example, an optically active 7-amino-5-azaspiro[2.4] heptane is a compound useful as an intermediate for synthetic antimicrobial agents that have high antibacterial activities.

Such an optically active 7-amino-5-azaspiro[2.4]heptane has been prepared by certain processes typically described in Japanese Unexamined Patent Application Publications No. 11-240867 and No. 11-240868. In these processes, an oxo group at the 7-position of a precursor 5-benzyl-4,7-dioxo-5-azaspiro[2.4]heptane is oximated with hydroxylamine, and an oxo group at the 4-position and a hydroxyimino group at the 7-position are reduced to yield 7-amino-5-benzyl-5-azaspiro[2.4]heptane, the 7-amino-5-benzyl-5-azaspiro[2.4]heptane is then condensed with an optically active carboxylic acid and is converted into a 5-benzyloxycarbonyl derivative, the resulting diastereomers are separated and are deprotected to thereby yield an optically active 7-amino-5-azaspiro[2.4]heptane.

These publications also describe a process for the preparation of an optically active 7-amino-5-azaspiro[2.4]heptane derivative, in which an optically active 1-phenylethyl group is introduced, instead of the benzyl group, at the 5-position of 5-benzyl-4,7-dioxo-5-azaspiro[2.4]heptane, the oxo group at the 7-position of the resulting compound is converted into an amino group, and the resulting diastereomers are separated to thereby yield the target compound.

In all of these processes, however, diastereomers are once prepared synthetically and are then subjected to resolution. The processes are thereby low in yields and are not efficient for the preparation of an optically active 7-amino-5-azaspiro [2.4]heptane.

SUMMARY OF THE INVENTION

Accordingly, an object of the present invention is to provide a process for the efficient preparation of optically active 7-amino-5-azaspiro[2.4]heptane derivative and other optically active amines or salts thereof.

Another object of the present invention is to provide a process for the efficient preparation of optically active imines that are useful for the preparation of optically active amines or salts thereof.

A further object of the present invention is to provide novel optically active amines or salts thereof and novel optically active imines that are useful typically as intermediates for medical drugs and agricultural chemicals.

After intensive investigations, the present inventors have found that a corresponding optically active primary amine can efficiently be obtained by reacting a ketone with a specific optically active primary amine in the presence of an organic acid to yield a corresponding imine, asymmetrically hydrogenating the imine to thereby yield an optically active secondary amine, and subjecting the optically active secondary amine to hydrogenation (hydrogenolysis) to thereby yield the target compound corresponding to the ketone. The present invention has been accomplished based on these findings.

Specifically, the present invention provides, in an aspect, a process for the preparation of an optically active amine or a salt thereof, the process including the steps of:

(A1) reacting a ketone of following Formula (1a):

$$\underset{R^{2a}}{\overset{R^{1}}{\diagdown}}C=O \tag{1a}$$

wherein $R^1$ is an unsubstituted or substituted hydrocarbon group; and $R^{2a}$ is a hydrocarbon group having at least one oxo group and optionally having other substituent, or $R^1$ and $R^{2a}$ may, together with the adjacent carbon atom, be combined with or without an intervening hetero atom to form an unsubstituted or substituted ring, with an optically active amine of following Formula (2):

$$H_2N\underset{R^4}{\overset{\displaystyle R^3}{\diagdown}}C^1H \tag{2}$$

wherein $R^3$ is an unsubstituted or substituted aryl group; $R^4$ is an unsubstituted or substituted lower alkyl group; and $C^1$ is an asymmetric carbon atom, in the presence of an organic acid to thereby yield an optically active imine of following Formula (3a):

$$\underset{R^{2a}}{\overset{R^{1}}{\diagdown}}C=N\underset{R^4}{\overset{\displaystyle R^3}{\diagdown}}C^1H \tag{3a}$$

wherein $R^1$, $R^{2a}$, $R^3$, $R^4$, and $C^1$ have the same meanings as defined above;

(B1) hydrogenating the optically active imine of Formula (3a) in the presence of a catalyst to thereby yield an optically active amine of following Formula (4a):

$$\underset{R^{2a}}{\overset{R^{1}}{\diagdown}}C^2H-\underset{}{\overset{H}{\underset{N}{|}}}\underset{R^4}{\overset{\displaystyle R^3}{\diagdown}}C^1H \tag{4a}$$

wherein $R^1$, $R^{2a}$, $R^3$, $R^4$, and $C^1$ have the same meanings as defined above; and $C^2$ is an asymmetric carbon atom;

(C1) hydrogenating the optically active amine of Formula (4a) or a salt thereof in the presence of a catalyst to thereby yield an optically active amine of following Formula (5a):

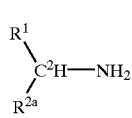

(5a)

wherein $R^1$, $R^{2a}$, and $C^2$ have the same meaning as defined above, or a salt thereof; and (D) reducing the optically active amine of Formula (5a) or a salt thereof with a reducing agent to thereby yield an optically active amine of following Formula (6):

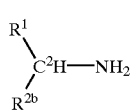

(6)

wherein $R^{2b}$ is a group corresponding to the group $R^{2a}$ except with a hydrogen atom replacing the oxo group of $R^{2a}$; and $R^1$ and $C^2$ have the same meanings as defined above, or a salt thereof.

Organic acids for use in the step (A1) in the above process include, for example, acetic acid. The reducing agent in the step (D) may be sodium bis(2-methoxyethoxy) aluminum hydride. It is preferred that (i) $C^1$ is an asymmetric carbon atom with the R-configuration and $C^2$ is an asymmetric carbon atom with the S-configuration. It is also preferred that (ii) $C^1$ is an asymmetric carbon atom with the S-configuration and $C^2$ is an asymmetric carbon atom with the R-configuration. The ketones of Formula (1a) include, for example, cyclic ketones each having an amide bond and a ketonic carbonyl group on its ring. The ketones of Formula (1a) also include compounds of following Formula (7):

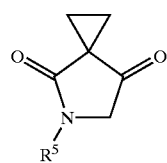

(7)

wherein $R^5$ is an unsubstituted or substituted aryl-lower alkyl group. In this case, it is preferred that $R^3$ and $R^4$ in Formula (2) are a phenyl group and a methyl group, respectively, and $R^5$ in Formula (7) is a benzyl group.

In another aspect, the present invention provides a process for the preparation of an optically active amine or a salt thereof, the process including the steps of:

(A) reacting a ketone of following Formula (1):

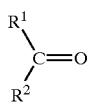

(1)

wherein $R^1$ and $R^2$ are different from each other and are each an unsubstituted or substituted hydrocarbon group, or $R^1$ and $R^2$ may, together with the adjacent carbon atom, be combined with or without an intervening hetero atom to form an unsubstituted or substituted ring, with an optically active amine of following Formula (2):

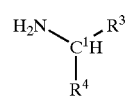

(2)

wherein $R^3$ is an unsubstituted or substituted aryl group; $R^4$ is an unsubstituted or substituted lower alkyl group; and $C^1$ is an asymmetric carbon atom, in the presence of an organic acid to thereby yield an optically active imine of following Formula (3):

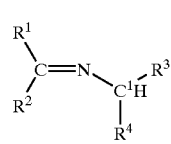

(3)

wherein $R^1$, $R^2$, $R^3$, $R^4$, and $C^1$ have the same meanings as defined above;

(B) hydrogenating the optically active imine of Formula (3) in the presence of a catalyst to thereby yield an optically active amine of following Formula (4):

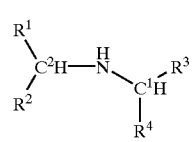

(4)

wherein $R^1$, $R^2$, $R^3$, $R^4$, and $C^1$ have the same meanings as defined above; and $C^2$ is an asymmetric carbon atom; and (C) hydrogenating the optically active amine of Formula (4) or a salt thereof in the presence of a catalyst to thereby yield an optically active amine of following Formula (5):

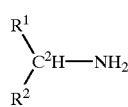

(5)

wherein $R^1$, $R^2$, and $C^2$ have the same meanings as defined above, or a salt thereof.

In the above process, organic acids for use in the step (A) include, for example, acetic acid. It is preferred that (i) $C^1$ is an asymmetric carbon atom with the R-configuration and $C^2$ is an asymmetric carbon atom with the S-configuration. It is also preferred that (ii) $C^1$ is an asymmetric carbon atom with the S-configuration and $C^2$ is an asymmetric carbon atom with the R-configuration. The ketones of Formula (1) include, for example, cyclic ketones each having a nitrogen atom and a ketonic carbonyl group on its ring. The ketones of Formula (1) also include compounds of following Formulae (7) and (8):

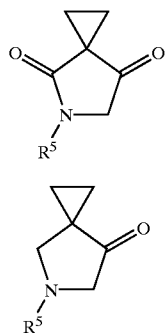

wherein R⁵ is an unsubstituted or substituted aryl-lower alkyl group. In this case, it is preferred that R³ and R⁴ in Formula (2) are a phenyl group and a methyl group, respectively, and R⁵ in Formulae (7) and (8) is a benzyl group.

The present invention also provides, in a further aspect, a process for the preparation of an optically active amine, the process including the steps of:

(A) reacting a ketone of following Formula (1):

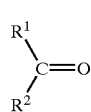

wherein R¹ and R² are different from each other and are each an unsubstituted or substituted hydrocarbon group, or R¹ and R² may, together with the adjacent carbon atom, be combined with or without an intervening hetero atom to form an unsubstituted or substituted ring, with an optically active amine of following Formula (2):

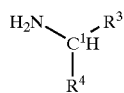

wherein R³ is an unsubstituted or substituted aryl group; R⁴ is an unsubstituted or substituted lower alkyl group; and C¹ is an asymmetric carbon atom, in the presence of an organic acid to thereby yield an optically active imine of following Formula (3):

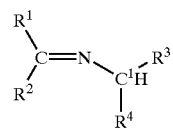

wherein R¹, R², R³, R⁴, and C¹ have the same meanings as defined above; and (B) hydrogenating the optically active imine of Formula (3) in the presence of a catalyst to thereby yield an optically active amine of following Formula (4):

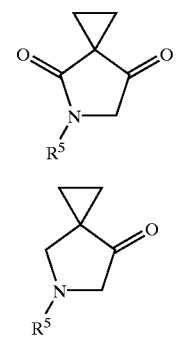

wherein R¹, R², R³, R⁴, and C¹ have the same meanings as defined above; and C² is an asymmetric carbon atom.

In the above process, organic acids for use in the step (A) include, for example, acetic acid. It is preferred that (i) C¹ is an asymmetric carbon atom with the R-configuration and C² is an asymmetric carbon atom with the S-configuration. It is also preferred that (ii) C¹ is an asymmetric carbon atom with the S-configuration and C² is an asymmetric carbon atom with the R-configuration. The ketones of Formula (1) include, for example, cyclic ketones each having a nitrogen atom and a ketonic carbonyl group on its ring. The ketones of Formula (1) also include compounds of following Formulae (7) and (8):

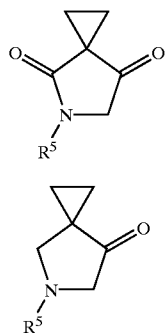

wherein R⁵ is an unsubstituted or substituted aryl-lower alkyl group. In this process, it is preferred that R³ and R⁴ in Formula (2) are a phenyl group and a methyl group, respectively, and R⁵ in Formulae (7) and (8) is a benzyl group.

The present invention provides, in another aspect, optically active amines of following Formulae (9) and (10):

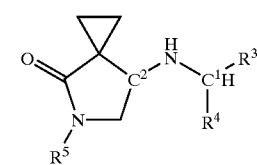

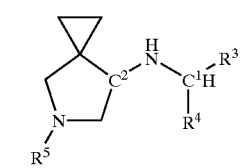

wherein R³ is an unsubstituted or substituted aryl group; R⁴ is an unsubstituted or substituted lower alkyl group; R⁵ is an unsubstituted or substituted aryl-lower alkyl group; and C¹ and C² are each an asymmetric carbon atom, and salts thereof. In these compounds, it is preferred that R³ is a phenyl group, R⁴ is a methyl group, and R⁵ is a benzyl group.

Also provided is a process for the preparation of an optically active imine, the process including the step of:

(A) reacting a ketone of following Formula (1):

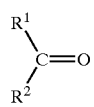
(1)

wherein $R^1$ and $R^2$ are different from each other and are each an unsubstituted or substituted hydrocarbon group, or $R^1$ and $R^2$ may, together with the adjacent carbon atom, be combined with or without an intervening hetero atom to form an unsubstituted or substituted ring, with an optically active amine of following Formula (2):

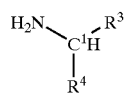
(2)

wherein $R^3$ is an unsubstituted or substituted aryl group; $R^4$ is an unsubstituted or substituted lower alkyl group; and $C^1$ is an asymmetric carbon atom, in the presence of an organic acid to thereby yield an optically active imine of following Formula (3):

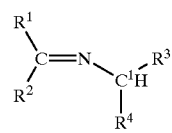
(3)

wherein $R^1$, $R^2$, $R^3$, $R^4$, and $C^1$ have the same meanings as defined above.

In the above process, organic acids for use in the step (A) include, for example, acetic acid. The asymmetric carbon atom $C^1$ may be one with the R-configuration or may be one with the S-configuration. The ketones of Formula (1) include, for example, cyclic ketones each having a nitrogen atom and a ketonic carbonyl group on its ring. The ketones of Formula (1) also include compounds of following Formulae (7) and (8):

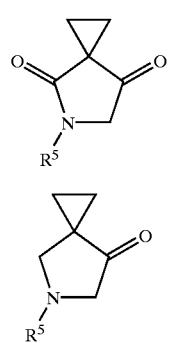
(7)

(8)

wherein $R^5$ is an unsubstituted or substituted aryl-lower alkyl group. It is preferred that $R^3$ and $R^4$ in Formula (2) are a phenyl group and a methyl group, respectively, and $R^5$ in Formulae (7) and (8) is a benzyl group.

Also provided are optically active imines of following Formulae (11) and (12):

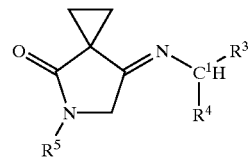
(11)

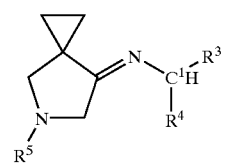
(12)

wherein $R^3$ is an unsubstituted or substituted aryl group; $R^4$ is an unsubstituted or substituted lower alkyl group; $R^5$ is an unsubstituted or substituted aryl-lower alkyl group; and $C^1$ is an asymmetric carbon atom. In these compounds, it is preferred that $R^3$ is a phenyl group, $R^4$ is a methyl group, and $R^5$ is a benzyl group.

In addition and advantageously, the present invention provides a process for the preparation of an optically active amine or a salt thereof, the process comprising the step of:

(D) reducing an optically active amine of following Formula (5a)

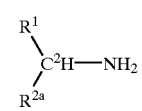
(5a)

wherein $R^1$ is an unsubstituted or substituted hydrocarbon group; $R^{2a}$ a hydrocarbon group having at least one oxo group and optionally having other substituent, or $R^1$ and $R^{2a}$ may, together with the adjacent carbon atom, be combined with or without an intervening hetero atom to form an unsubstituted or substituted ring; and $C^2$ is an asymmetric carbon atom, or a salt thereof, with a reducing agent to thereby yield an optically active amine of following Formula (6):

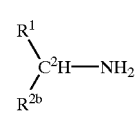
(6)

wherein $R^{2b}$ is a group corresponding to the group $R^{2a}$ except with a hydrogen atom replacing the oxo group of $R^{2a}$; and $R^1$ and $C^2$ have the same meanings as defined above, or a salt thereof.

In the above process, reducing agents for use in the step (D) include, for example, sodium bis(2-methoxyethoxy) aluminum hydride. The asymmetric carbon atom $C^2$ may be one with the S-configuration or one with the R-configuration. In the optically active amine of Formula (5a), $R^1$ and $R^{2a}$ may together with the adjacent carbon atom $C^2$ be combined with an intervening nitrogen atom to form a lactam ring. The optically active amines of Formula (5a) include, for example, compounds of following Formula (13):

(13)

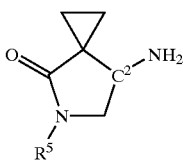

wherein $R^5$ is an unsubstituted or substituted aryl-lower alkyl group; and $C^2$ is an asymmetric carbon atom. $R^5$ may be a benzyl group.

The processes of the present invention can efficiently produce optically active amines or salts thereof that are useful typically as intermediates for medical drugs and agricultural chemicals. They can also efficiently produce optically active imines that are useful for the preparation of the optically active amines or salts thereof.

In addition, the present invention provides novel optically active amines or salts thereof and novel optically active imines that are useful typically as intermediates for medical drugs and agricultural chemicals.

DESCRIPTION OF THE PREFERRED EMBODIMENTS

[Step (A1) and Step (A)]

In the step (A1), the ketone of Formula (1a) is reacted with the optically active amine of Formula (2) in the presence of an organic acid and thereby yields an optically active imine of Formula (3a). In the step (A), the ketone of Formula (1) is reacted with the optically active amine of Formula (2) in the presence of an organic acid and thereby yields an optically active imine of Formula (3).

In Formulae (1a) and (1), examples of hydrocarbon groups in $R^1$, $R^{2a}$, and $R^2$ include aliphatic hydrocarbon groups, alicyclic hydrocarbon groups, aromatic hydrocarbon groups, and groups each comprising a plurality of these groups combined with each other. Such aliphatic hydrocarbon groups include, but are not limited to, methyl, ethyl, propyl, isopropyl, butyl, isobutyl, t-butyl, pentyl, isopentyl, hexyl, and other straight- or branched-chain alkyl groups each containing from one to six carbon atoms. The alicyclic hydrocarbon groups include, but are not limited to, cyclopropyl, cyclobutyl, cyclopentyl, cyclohexyl, and other cycloalkyl groups. The aromatic hydrocarbon groups include, but are not limited to, phenyl, and naphthyl groups. Groups each comprising an alicyclic hydrocarbon group and an aliphatic hydrocarbon group combined with each other include, but are not limited to, cyclopropylmethyl, cyclohexylmethyl, and other cycloalkyl-$C_1$–$C_6$ alkyl groups; 1-methylcycloprop-1-yl, 1-methylcyclohex-1-yl, and other $C_1$–$C_6$ alkyl-cycloalkyl groups. Groups each comprising an aromatic hydrocarbon group and an aliphatic hydrocarbon group combined with each other include, but are not limited to, benzyl, phenethyl, naphthylmethyl, and other aryl-lower alkyl groups (aryl-substituted $C_1$–$C_6$ alkyl groups); and tolyl, xylyl, and other lower alkyl-substituted aryl groups ($C_1$–$C_6$ alkyl-substituted aryl groups).

The hydrocarbon groups may have one or more substituents. Such substituents are not specifically limited, as long as they do not adversely affect reactions, and include, for example, fluorine, chlorine, bromine, and other halogen atoms; lower alkoxy groups such as methoxy, ethoxy, propoxy, isopropoxy, butoxy, t-butoxy, pentyloxy, hexyloxy, and other $C_1$–$C_6$ alkoxy groups, and other lower alkoxy groups; oxo group; nitro group; cyano group; hydroxyl groups which may be protected by a protecting group; amino groups which may be protected by a protecting group; carboxyl groups (e.g., carboxyl group, and alkoxycarbonyl groups) which may be protected by a protecting group; heterocyclic groups; and substituents each comprising a plurality of these groups combined with each other. The protecting groups mentioned herein and hereinafter include protecting groups conventionally used in the field of organic synthesis.

The hydrocarbon group in $R^{2a}$ has at least an oxo group and may have one or more substituents in addition to the oxo group. The oxo group may be any oxo group such as an oxo group of a ketonic carbonyl group, an oxo group of a carbonyl group constituting an amide, an oxo group of a carbonyl group constituting an ester, an oxo group of a carbonyl group constituting a carbonate, and an oxo group of a carbonyl group constituting urea. The oxo group is preferably an oxo group of a carbonyl group constituting an amide.

The substituents $R^1$ and $R^{2a}$, or $R^1$ and $R^2$ may, together with the adjacent carbon atom (a carbonyl carbon), be combined with or without an intervening hetero atom to form a ring. Examples of such hetero atoms are a nitrogen atom, an oxygen atom, and a sulfur atom. The nitrogen atom may have a substituent (inclusive of a protecting group). Such substituents (inclusive of protecting groups) include, but are not limited to, alkyl groups such as methyl, ethyl, and other $C_1$–$C_6$ alkyl groups; aralkyl groups such as benzyl group which may have a substituent (e.g., $C_1$–$C_4$ alkyl groups, $C_1$–$C_4$ alkoxy group, nitro group, cyano group, and halogen atoms); acyl groups such as acetyl, benzoyl, and other $C_1$–$C_{10}$ acyl groups; and aryloxycarbonyl groups such as benzyloxycarbonyl group. Preference is given to protecting groups as the substituent for the nitrogen atom, of which protecting groups that can be decomposed and removed by hydrogenation, such as unsubstituted or substituted benzyl group, and benzyloxycarbonyl group, are typically preferred.

Rings, if any, formed from $R^1$ and $R^{2a}$, or $R^1$ and $R^2$ include, but are not limited to, cyclopentane ring, cyclohexane ring, cycloheptane ring, cyclooctane ring, and other cycloalkane rings; oxolane ring, oxane ring, oxepane ring, and other oxygen-atom-containing heterocyclic rings; thioxolane ring, thioxane ring, and other sulfur-atom-containing heterocyclic rings; pyrrolidine ring, piperidine ring, hydroazepine ring, quinuclidine ring, and other nitrogen-atom-containing heterocyclic rings. These rings may have substituents such as those the hydrocarbon groups may have. Other hydrocarbon rings or heterocyclic rings may be condensed or combined with these rings by commonly possessing one or more atoms to thereby form bridged rings or spiro rings.

Examples of ketones in which $R^1$ and $R^{2a}$ or $R^1$ and $R^2$ form a ring are cycloheptanone or derivatives thereof, and other cycloalkanone derivatives; quinuclidinone or derivatives thereof, 4,7-dioxo-5-azaspiro[2.4]heptane or derivatives thereof, 7-oxo-5-azaspiro[2.4]heptane or derivatives thereof, and other cyclic ketones each having a nitrogen atom and a ketonic carbonyl group on its ring. The nitrogen atom just mentioned above may have any of the above protecting groups and other substituents combined therewith. Among them, examples of ketones in which $R^1$ and $R^{2a}$ form a ring include 4,7-dioxo-5-azaspiro[2.4]heptane or derivatives thereof, and other cyclic ketones each having an amide bond and a ketonic carbonyl group on its ring. The nitrogen atom constituting the amide bond may have any of the aforementioned protecting groups and other substituents.

Examples of 4,7-dioxo-5-azaspiro[2.4]heptane derivatives include the compounds of Formula (7). Examples of 7-oxo-5-azaspiro[2.4]heptane derivatives include the compounds of Formula (8). In Formulae (7) and (8), aryl-lower alkyl groups in $R^5$ include, for example, benzyl group, 1-phenylethyl group, trityl group, naphthylmethyl group, and other 1-aryl-$C_1$–$C_6$ alkyl groups, and other groups that can be decomposed and removed by hydrogenation. These aryl-lower alkyl groups may have one or more substituents. Such substituents which the aryl moiety may have include, but are not limited to, $C_1$–$C_4$ alkyl groups, $C_1$–$C_4$ alkoxy groups, nitro group, cyano group, and halogen atoms. As $R^5$, benzyl group is typically preferred.

In the optically active amines of Formula (2), the "unsubstituted or substituted aryl group" in $R^3$ includes, for example, phenyl, and naphthyl groups which may have any of the substituents exemplified as those the hydrocarbon groups may have. The "unsubstituted or substituted lower alkyl group" in $R^4$ includes, for example, alkyl groups each containing from one to six carbon atoms which may have any of the substituents exemplified as those the hydrocarbon groups may have.

Examples of the optically active amines of Formula (2) are (R)-αn-phenethylamine, (S)-α-phenethylamine, (R)-1-(1-naphthyl)ethylamine, and (S)-1-(1-naphthyl)ethylamine.

Organic acids are used as a catalyst in the steps (A1) and (A) Such organic acids include, but are not limited to, acetic acid, propionic acid, butyric acid, oxalic acid, malonic acid, and other organic carboxylic acids; p-toluenesulfonic acid, benzenesulfonic acid, naphthalenesulfonic acid, methanesulfonic acid, trifluoromethanesulfonic acid, sulfonic acid-type cation exchange resins, and other sulfonic acids. Among them, organic carboxylic acids are preferred, of which acetic acid is typically preferred.

The amount of catalyst can appropriately be set and is, if acetic acid is used, typically from about 0.1 to about 3.0 moles, and preferably from about 0.5 to about 1.5 moles, per mole of the ketone of Formula (1a) or (1).

Solvents for use in the reaction are not specifically limited as long as they do not adversely affect the progress of reaction. Such solvents include, but are not limited to, hexane, and other aliphatic hydrocarbons; cyclohexane, and other alicyclic hydrocarbons; benzene, toluene, xylenes, ethylbenzene, and other aromatic hydrocarbons; methylene chloride, and other halogenated hydrocarbons; diethyl ether, dimethoxyethane, tetrahydrofuran, and other chain or cyclic ethers; ethyl acetate, and other esters; ethanol, and other alcohols; and mixtures of these solvents. Among them, preference is given to toluene, and other solvents from which by-produced water can be removed by azeotropy.

The amount of solvent is not critical, and is from about 3 to about 20 times by weight, and preferably from about 5 to about 8 times by weight that of the ketone used as a raw material.

The amount of the optically active amine of Formula (2) is preferably from about 1.0 to about 5.0, and more preferably from about 1.0 to about 2.0 moles per mole of the ketone.

The reaction temperature is not critical and can be, for example, within the range of from about 30° C. to about 80° C., and preferably from about 50° C. to about 60° C. Water is produced as a by-product with the progress of reaction. The by-produced water can be removed by azeotropy with the solvent during or after the reaction. Alternatively, a dehydrating agent (a water-adsorbent) is added to the reaction system to capture the by-produced water.

As a result of the reaction, a corresponding optically active imine of Formula (3a) or (3) is formed. Reaction products can be separated and purified after the completion of the reaction by separation and purification means such as filtration, concentration, distillation, extraction, crystallization, recrystallization, adsorption, and column chromatography, and any combination of these separation and purification means. Alternatively, they can be subjected to a subsequent process step without isolation.

The optically active imine of Formula (11) or (12) of the present invention can be obtained by reacting the ketone of Formula (7) or (8) with the optically active amine of Formula (2) in the presence of an organic acid according to the aforementioned process. Preferred imines include those in which $R^3$ is phenyl, $R^4$ is methyl, and $R^5$ is a protecting group that can be decomposed and removed by hydrogenation, typically benzyl group.

[Step (B1) and Step (B)]

In the step (B1), the optically active imine of Formula (3a) is hydrogenated in the presence of a catalyst and thereby yields a corresponding optically active amine of Formula (4a). Likewise, in the step (B), the optically active imine of Formula (3) is hydrogenated in the presence of a catalyst and thereby yields a corresponding optically active amine of Formula (4).

Metal catalysts (catalysts comprising elementary metals or metal compounds) that are effective for hydrogenation can be used as the catalyst. Such metal catalysts include, but are not limited to, platinum catalysts, palladium catalysts, rhodium catalysts, iridium catalysts, ruthenium catalysts, and nickel catalysts. Among them, platinum catalysts are preferred, of which platinum (IV) oxide is typically preferred. The amount of the metal catalyst is typically from about 0.01 to about 0.2 time by weight, and preferably from about 0.05 to about 0.1 time by weight the charged amount of the raw material imine of Formula (3a) or (3).

The reaction can be performed in the presence of a solvent. Such solvents are not specifically limited as long as they do not adversely affect the progress of reaction. Examples of preferred solvents are alcohols such as methanol, ethanol, propanol, and isopropyl alcohol. The amount of the solvent is typically from about 3 to about 30 times by weight, and preferably from about 5 to about 20 times by weight the charged amount of the imine of Formula (3a) or (3).

The reaction pressure can be selected within the range of typically from about 1 to about 100 atm (from about 0.1 to about 10 MPa), and preferably from about 1 to about 10 atm (from about 0.1 to about 1 MPa). The reaction can be performed in the presence of, or under the flow of hydrogen. The gas phase of the reaction system may further comprise an inert gas such as nitrogen, argon, and helium gas in addition to hydrogen gas. To enhance gas-liquid contact, a hydrogen-containing gas may be blown into the liquid phase of the reaction system using a blowing tube. The reaction temperature is not critical as long as it is equal to or higher than the melting point of the system and lower than or equal to its boiling point. The temperature is preferably from about 10° C. to about 30° C.

As a result of the reaction, the optically active imine of Formula (3a) or (3) is hydrogenated on its carbon-nitrogen double bond and thereby yields a corresponding optically active amine of Formula (4a) or (4b). For example, hydrogenation of the optically active imines of Formulae (11) and (12) yields corresponding optically active amines of Formulae (9) and (10), respectively.

In this process step, the configuration around the asymmetric carbon atom $C^1$ of the imine of Formula (3a) or (3) controls the configuration of an asymmetric carbon atom $C^2$ formed as a result of hydrogenation to thereby yield one of two possible diastereomers selectively. In other words, the structures of $R^1$, $R^{2a}$, and $R^2$ and the configuration of the asymmetric carbon atom $C^1$ serve to yield selectively either of an amine having $C^1$ with the R-configuration and $C^2$ with the S-configuration and an amine having $C^1$ with the R-configuration and $C^2$ with the R-configuration, or to yield selectively either of an amine having $C^1$ with the S-configuration and $C^2$ with the R-configuration and amine having $C^1$ with the S-configuration and $C^2$ with the S-configuration.

In particular, one of two diastereomers is formed with high selectivity when $R^1$ and/or $R^{2a}$, or $R^1$ and/or $R^2$ in Formula (3a) or (3) is a bulky group or when $R^1$ and $R^{2a}$ or $R^1$ and $R^2$ are combined, with or without an intervening hetero atom, to form a ring together with the adjacent carbon atom.

More specifically, hydrogenation of an imine [e.g., an imine of Formula (11)] obtained as a result of the reaction between a 5-substituted-4,7-dioxo-5-azaspiro[2.4]heptane derivative (e.g., a 5-hydrocarbon group-substituted-4,7-dioxo-5-azaspiro[2.4]heptane derivative) and an α-phenethylamine yields, if the α-phenethylamine is (R)-α-phenethylamine, an amine having the 7-position with the S-configuration, namely, (7S,1'R)-7-(1-phenylethylamino)-4-oxo-5-substituted-5-azas piro[2.4]heptane derivative, selectively. If the α-phenethylamine is (S)-α-phenethylamine, the hydrogenation yields an amine having the 7-position with the R-configuration, namely (7R,1'S)-7-(1-phenylethylamino)-4-oxo-5-substituted-5-azas piro[2.4] heptane derivative, selectively. Likewise, hydrogenation of an imine [e.g., an imine of Formula (12)] obtained as a result of the reaction between a 5-substituted-7-oxo-5-azaspiro [2.4]heptane derivative (e.g., a 5-hydrocarbon group-substituted-7-oxo-5-azaspiro[2.4]heptane derivative) and an α-phenethylamine selectively yields, if the α-phenethylamine is (R)-α-phenethylamine, an amine having the 7-position with the S-configuration, namely, (7S, 1'R)-7-(1-phenylethylamino)-5-substituted-5-azaspiro[2.4] heptane derivative. If the α-phenethylamine is (S)-α-phenethylamine, the hydrogenation selectively yields an amine having the 7-position with the R-configuration, namely (7R,1'S)-7-(1-phenylethylamino)-5-substituted-5-azaspiro[2.4]heptane derivative.

The 5-substituted-4,7-dioxo-5-azaspiro[2.4]heptane derivative can be prepared according to procedures described in Japanese Unexamined Patent Application Publications No. 11-240867 and No. 11-240868. The 5-substituted-7-oxo-5-azaspiro[2.4]heptane derivative (e.g. 5-hydrocarbon group-substituted-7-oxo-5-azaspiro[2.4] heptane derivative) can be prepared by reducing a carbonyl group at the 4-position of the 5-substituted-4,7-dioxo-5-azaspiro[2.4]heptane derivative with a reducing agent that can reduce an amide to an amine.

Reaction products can be separated and purified after the completion of reaction by separation and purification means such as filtration, concentration, distillation, extraction, crystallization, recrystallization, adsorption, and column chromatography, and any combination of these separation and purification means. Alternatively, they can be subjected to a subsequent process step without isolation.

[Step (C1) and Step (C)]

In the step (C1), the optically active amine of Formula (4a) or a salt thereof is hydrogenated in the presence of a catalyst and thereby yields an optically active amine of Formula (5a) or a salt thereof. In the Step (C), the optically active amine of Formula (4) or a salt thereof is hydrogenated in the presence of a catalyst and thereby yields an optically active amine of Formula (5) or a salt thereof.

The "salts of the amine compounds" herein mean and include salts of inorganic acids and salts of organic acids. Such inorganic acid include, but are not limited to, hydrochloric acid, sulfuric acid, nitric acid, phosphoric acid, and boric acid. Such organic acids include, but are not limited to, acetic acid, propionic acid, butyric acid, oxalic acid, malonic acid, and other organic carboxylic acids; p-toluenesulfonic acid, benzenesulfonic acid, naphthalenesulfonic acid, methanesulfonic acid, trifluoromethanesulfonic acid, and other sulfonic acids. These salts of amines and free amines can be converted into each other according to a conventional procedure.

Catalysts for use herein are catalysts that can subject benzyl groups to hydrogenolysis, such as a palladium-carbon catalyst. The amount of the palladium born on the palladium-carbon catalyst is from about 1% to about 30% by weight, and preferably from about 5% to about 10% by weight based on the carbon weight. The amount of the catalyst is from about 0.01 to about 20 times by weight, and preferably from about 0.1 to about 10 times by weight that of the amine compound of Formula (4a) or (4).

Reaction solvents for use herein are not specifically limited as long as they do not adversely affect the progress of reaction, of which alcohols are preferred. Such alcohols include, but are not limited to, methanol, ethanol, propanol, and isopropyl alcohol. Each of the solvents can be used alone or in combination. The amount of the solvent is, for example, from about 3 to about 50 times by weight, and preferably from about 5 to about 10 times by weight that of the amine of Formula (4a) or (4) or a salt thereof.

In this reaction, addition of an acid to the reaction system can reduce the amount of the palladium-carbon catalyst. Such acids include, but are not limited to, hydrochloric acid, hydrobromic acid, and hydroiodic acid, of which hydrochloric acid is preferred. The concentration of hydrochloric acid is generally from about 5% to about 35% by weight, and preferably from about 10% to about 35% by weight. The amount of the acid such as hydrochloric acid is from about 0.2 to about 3.0 moles, and preferably from about 0.8 to about 2.0 moles per mole of the amine of Formula (4a) or (4) or a salts thereof. By using hydrochloric acid as the acid, the amount of the palladium-carbon catalyst can be reduced to one tenth or lower that in the case in which hydrochloric acid is not used.

When the acid is added to the reaction system, the amine of Formula (5a) or (5) is obtained in the salt form. By treating the salt with an appropriate base, a free amine can be obtained. Such bases include, but are not limited to, sodium carbonate, potassium carbonate, and other alkali metal carbonates; sodium hydrogencarbonate, potassium hydrogencarbonate, and other alkali metal hydrogencarbonates; sodium hydroxide, potassium hydroxide, and other alkali metal hydroxides; magnesium carbonate, calcium carbonate, and other alkaline earth metal carbonates; magnesium hydroxide, calcium hydroxide, and other alkaline earth metal hydroxides; and other inorganic bases. Each of these bases can be used alone or in combination.

The reaction pressure is typically from about 1 to about 100 atm (from about 0.1 to about 10 MPa), and preferably from about 2 to about 30 atm (from about 0.2 to about 3 MPa). The gas phase of the reaction system may further comprise an inert gas such as nitrogen, argon, and helium gas in addition to hydrogen gas. To enhance gas-liquid contact, a hydrogen-containing gas may be blown into the liquid phase of the reaction system using a blowing tube. The reaction temperature is not critical, as long as it is equal to or higher than the melting point of the system, and is preferably from about 30° C. to about 100° C. The reaction time can be selected within the range of generally from about 2 to about 10 hours, and preferably from about 3 to about 5 hours, depending on the reaction temperature and other reaction conditions.

Hydrogenation (hydrogenolysis) of the optically active amines of Formulae (4a) and (4) or salts thereof yields corresponding optically active amines of Formulae (5a) and (5) or salts thereof, respectively. For example, hydrogenation of the optically active amine of Formula (9) yields an optically active amine of Formula (13).

Reaction products can be separated and purified after the completion of reaction by separation and purification means such as filtration, concentration, distillation, extraction, crystallization, recrystallization, adsorption, and column chromatography, and any combination of these separation and purification means. Alternatively, they can be subjected to a subsequent process step without isolation.

The resulting optically active amine of Formula (5a) or (5) can be converted into a salt and then into a crystal by the treatment with an appropriate acid according to a conventional procedure. Such acids for use herein include, for example, oxalic acid, malonic acid, acetic acid, and other organic acids. In addition, the optical purity of the optically active amine of Formula (5a) or (5) can be increased by converting the optically active amine into a salt with an optically active organic acid such as D- or L-tartaric acid, and D- or L-lactic acid, and crystallizing or recrystallizing the salt according to typically a procedure described in Japanese Unexamined Patent Application Publication No. 04-149174. For example, when a 7-amino-4-oxo-5-substituted-5-azaspiro[2.4]heptane derivative (e.g., a 7-amino-4-oxo-5-hydrocarbon group substituted-5-azaspiro[2.4]heptane derivative) is converted into a salt with L-tartaric acid, and the salt is crystallized, the target compound can be obtained with an optical purity of equal to or more than 99% e.e.

[Step (D)]

In the step (D), the optically active amine of Formula (5a) or a salt thereof is reduced with a reducing agent and thereby yields an optically active amine of Formula (6) or a salt thereof.

Reducing agents for use herein are not specifically limited, as long as they can convert (reduce) an oxo group in $R^{2a}$ of the amine of Formula (5a) or a salt thereof to a hydrogen atom, and include typically aluminum hydride complex compounds, and other metal-hydrogen complex compounds. Examples of the aluminum hydride complex compounds are lithium aluminum hydride ($LiAlH_4$), trialkoxy derivatives of lithium aluminum hydride [$LiAlH(OR)_3$, wherein R is an alkyl group], and sodium bis(2-methoxyethoxy)aluminum hydride [$NaAlH_2(OCH_2CH_2OCH_3)_2$]. Among them, trialkoxy derivatives of lithium aluminum hydride and sodium bis(2-methoxyethoxy) aluminum hydride are preferred for their low costs and high activities.

The amount of the reducing agent can be equal to or more than the equivalent amount to the optically active amine of Formula (5a) or a salt thereof. For example, if sodium bis(2-methoxyethoxy)aluminum hydride is used as the reducing agent, the amount is from about 1.0 to about 3.0 moles, and preferably from about 1.1 to about 1.8 moles per mole of the amine of Formula (5a) or a salt thereof. The reducing agent such as sodium bis (2-methoxyethoxy) aluminum hydride can be used in the form of solution in a solvent such as toluene.

Reaction solvents for use herein are not specifically limited, as long as they do not adversely affect the progress of reaction, of which aromatic hydrocarbons, and ethers are preferred. Such aromatic hydrocarbons include, but are not limited to, benzene, toluene, xylenes, and chlorobenzene, and such ethers include, but are not limited to, diethyl ether, t-butyl methyl ether, tetrahydrofuran, dioxane, and other chain or cyclic ethers. Each of these solvents can be used alone or in combination. Among them, toluene is particularly preferred. The amount of the solvent is typically from about 2 to about 20 times by weight, and preferably from about 3 to about 10 times by weight that of the amine of Formula (5a) or a salt thereof.

The reaction temperature is not critical as long as it is equal to or higher than the melting point of the system and is preferably from about 50° C. to about 90° C. The reaction time can be selected within the range of from about 10 minutes to about 3 hours, and preferably from about 20 minutes to about 1 hour, depending on the reaction temperature and other reaction conditions.

As a result of the reaction, an oxo group in $R^{2a}$ of the amine of Formula (5a) or a salt thereof is converted to a hydrogen atom (e.g., a carbonyl group is reduced to a methylene group) and thereby yields a corresponding optically active amine of Formula (6) or a salt thereof.

Reaction products can be separated and purified after the completion of the reaction by separation and purification means such as filtration, concentration, distillation, extraction, crystallization, recrystallization, adsorption, and column chromatography, and any combination of these separation and purification means.

The optically active imines and optically active amines or salts thereof prepared according to the processes of the present invention are useful typically as intermediates for medical drugs and agricultural chemicals. The optical purities of these optically active imines and optically active amines or salts thereof can be determined according to a conventional or known procedure. For example, the optical purity of the 7-amino-5-substituted-5-azaspiro[2.4]heptane derivative can be easily determined according to a procedure described in Japanese Unexamined Patent Application Publication No. 09-208561.

EXAMPLES

The present invention will be illustrated in further detail with reference to several examples below which are not intended to limit the scope of the specification, including the claims, in any manner. In the examples, NMP spectra were determined with tetramethylsilane as an internal standard at 270 MHz ($^1$H-NMR) using a nuclear magnetic resonance spectrometer JNM-EX270 available from JEOL Ltd. Coupling constants (Hz) are indicated by J. The abbreviation Ph means phenyl group.

Example 1

According to the following reaction formula, (R)-7-(1-phenylethylimino)-4-oxo-5-benzyl-5-azaspiro[2.4]h eptane was prepared.

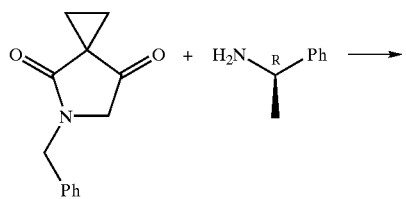

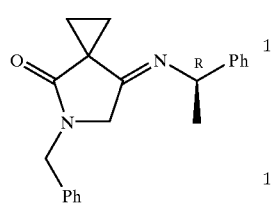

Specifically, 14.5 g of 5-benzyl-4,7-dioxo-5-azaspiro[2.4]heptane, 58 g of toluene, 16.3 g of (R)-α-phenethylamine, and 4.1 g of acetic acid were mixed and stirred at 60° C. for 2 hours. The mixture was then subjected to azeotropic dehydration at 60° C. at 100 mmHg (13.3 kPa) for 3hours. After the completion of reaction, the reaction mixture was filtrated, the filtrate was concentrated and thereby yielded 20 g of (R)-7-(1-phenylethylimino)-4-oxo-5-benzyl-5-azaspiro[2.4]h eptane.

$^1$H-NMR (CDCl$_3$) ppm: 1.37 (d, 3H, J=6.48, C$\underline{H}_3$), 1.42–1.59 (m, 4H, cyclopropyl), 3.83 (d, 1H, J=15.7, C$\underline{H}_2$), 4.03 (d, 1H, J=15.7, C$\underline{H}_2$), 4.30 (q, 1H, C$\underline{H}$), 4.45 (d, 1H, J=14.9, C$\underline{H}_2$), 4.73 (d, 1H, J=14.9, C$\underline{H}_2$), 7.18–7.38 (m, 10H, Ph)

Example 2

According to the following reaction formula, (7S,1'R)-7-(1-phenylethylamino)-4-oxo-5-benzyl-5-azaspiro[2.4]heptane was prepared.

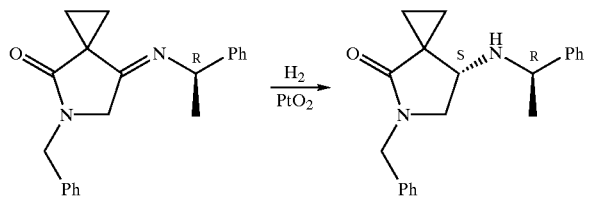

Specifically, 20 g of (R)-7-(1-phenylethylimino)-4-oxo-5-benzyl-5-azaspiro[2.4]h eptane prepared in Example 1, 160 g of methanol, and 0.2 g of platinum(IV) oxide were mixed, and after replacing the inside atmosphere of the system with hydrogen gas, the mixture was stirred at room temperature for 3 hours. After the completion of reaction, the reaction mixture was filtrated using a filter aid, was washed with 20 g of methanol, the filtrate was concentrated and thereby yielded 16.3 g of (7S,1'R)-7-(1-phenylethylamino)-4-oxo-5-benzyl-5-azaspiro[2.4]heptane with an optical purity of 79% d.e.

$^1$H-NMR (CDCl$_3$) ppm: 0.71–0.82 (m, 1H, cyclopropyl), 0.99–1.10 (m, 2H, cyclopropyl), 1.19–1.29 (m, 1H, cyclopropyl), 2.84 (dd, 1H, J=1.89, 6.75, C$\underline{H}_2$), 3.23–3.33 (m, 2H, C$\underline{H}_2$+C$\underline{H}$), 3.69 (q, 1H, J=6.48, C$\underline{H}$), 4.40 (s, 2H, C$\underline{H}_2$), 7.16–7.34 (m, 10H, Ph)

Example 3

According to the following reaction formula, (S)-7-amino-4-oxo-5-benzyl-5-azaspiro[2.4]heptane was prepared.

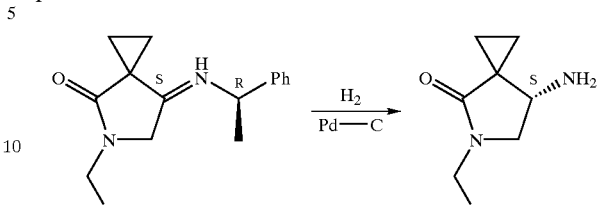

Specifically, 16 g of (7S,1'R)-7-(1-phenylethylamino)-4-oxo-5-benzyl-5-azaspiro[2.4]heptane prepared in Example 2, 128 g of methanol, and 5% by weight palladium-carbon were mixed, and after replacing the inside atmosphere of the system with hydrogen gas, and the mixture was stirred at 75° C. at a hydrogen pressure of 5 kgf/cm$^2$ (0.49 MPa) for 3 hours. After the completion of reaction, the reaction mixture was filtrated using a filter aid and was washed with 32 g of methanol. The filtrate was concentrated under reduced pressure and thereby yielded 10.5 g of (S)-7-amino-4-oxo-5-benzyl-5-azaspiro[2.4]heptane.

$^1$H-NMR (CDCl$_3$) ppm: 0.78–0.82 (m, 1H, cyclopropyl), 0.93–1.10 (m, 2H, cyclopropyl), 1.19–1.24 (m, 1H, cyclopropyl), 3.00 (dd, 1H, J=9.99, 4.05, C$\underline{H}_2$), 3.37 (dd, 1H, J=7.02, 4.05, C$\underline{H}_2$), 3.60 (q, 1H, J=9.99, 7.02, C$\underline{H}$), 4.50 (s, 2H, C$\underline{H}_2$), 7.23–7.37 (m, 5H, Ph)

Example 4

Preparation of (S)-7-amino-4-oxo-5-benzyl-5-azaspiro[2.4]heptane L-tartrate

A total of 10.5 g of (S)-7-amino-4-oxo-5-benzyl-5-azaspiro[2.4]heptane prepared in Example 3 was dissolved in 94.5 g of methanol, followed by addition of 1.75 g of L-tartaric acid. After the completion of dissolution, 0.01 g of crystalline (S)-7-amino-4-oxo-5-benzyl-5-azaspiro[2.4]heptane L-tartrate was added to the solution, followed by addition of 7.0 g of L-tartaric acid over 1 hour. Then, 47.3 g of diisopropyl ether was added dropwise over 1 hour. After completion of addition, the reaction mixture was cooled to 0° C. over 1 hour and was then stirred at 0° C. for 1 hour to form a crystal. The reaction mixture was filtrated, the crystal was washed with a mixture of 10.5 g of methanol and 5.3 g of diisopropyl ether, was dried under reduced pressure and thereby yielded 14.3 g of (S)-7-amino-4-oxo-5-benzyl-5-azaspiro[2.4]heptane L-tartrate.

The optical purity of the above-obtained (S)-7-amino-4-oxo-5-benzyl-5-azaspiro[2.4]heptane L-tartrate was determined in the following manner similar to a procedure described in Japanese Unexamined Patent Application Publication No. 09-208561.

To 21 mg of the (S)-7-amino-4-oxo-5-benzyl-5-azaspiro[2.4]heptane L-tartrate were added 1.6 g of toluene and 0.6 g of 20% by weight sodium hydroxide aqueous solution, the mixture was stirred and was then separated, and the toluene layer was concentrated. To the residue were added 50 mg of 3,5-dinitrobenzoyl chloride and 1 ml of tetrahydrofuran (THF). To the ice-cooled mixture was added dropwise 0.006 ml of triethylamine, followed by stirring at room temperature for 30 minutes to yield a N-3,5-dinitrobenzoyl derivative. The reaction mixture was diluted with saturated sodium hydrogencarbonate aqueous solution and chloroform and was then separated. The chloroform layer was analyzed by high performance liquid chromatography (HPLC).

HPLC Conditions

Column: SUMICHIRAL OA-4600 (4.6 mm in diameter, 250 mm in length)

Mobile phase: hexane/1,2-dichloroethane/ethanol=60/40/5

Detector: UV absorptiometer (254 nm)

Retention time: 7.5 min (S) and 12.9 min (R)

The result shows that the (S)-7-amino-4-oxo-5-benzyl-5-azaspiro[2.4]heptane L-tartrate has an optical purity of 99.4% e.e.

Example 5

Preparation of (S)-7-amino-4-oxo-5-benzyl-5-azaspiro[2.4]heptane

To 14.3 g of (S)-7-amino-4-oxo-5-benzyl-5-azaspiro[2.4]heptane L-tartrate prepared in Example 4 was added and stirred 85.8 g of toluene, followed by dropwise addition of 23.4 g of 20% by weight sodium hydroxide aqueous solution at a temperature of 30° C. or lower. After separation, the toluene layer was adjusted to have pH11.6 to 12.0 with a concentrated hydrochloric acid, was concentrated under reduced pressure and thereby yielded 6.3 g of (S)-7-amino-4-oxo-5-benzyl-5-azaspiro[2.4]heptane.

Example 6

According to the following reaction formula, (S)-7-amino-5-benzyl-5-azaspiro[2.4]heptane was prepared.

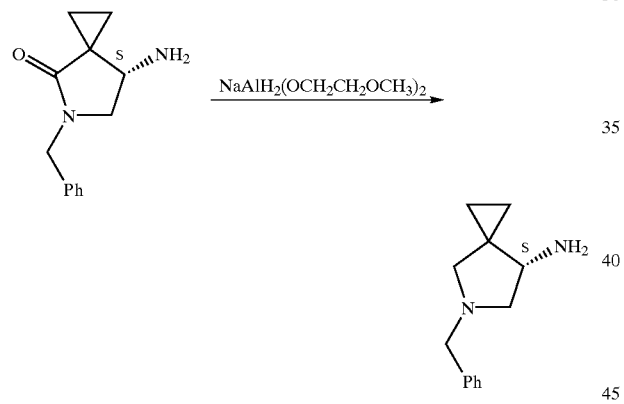

Specifically, 6.3 g of (S)-7-amino-4-oxo-5-benzyl-5-azaspiro[2.4]heptane prepared in Example 5 was added to 31.5 g of toluene and was stirred at 45° C. To the mixture was added dropwise a mixture of 10.9 g of 65% by weight solution of sodium bis (2-methoxyethoxy) aluminum hydride in toluene and 12.6 g of toluene at a temperature of 75° C. or lower within 5 minutes. After the completion of addition, the mixture was stirred at 75° C. for 30 minutes and was cooled to 5° C. or below. To the cooled mixture was added 124.4 g of 10% by weight hydrochloric acid at a temperature of 20° C. or lower, the mixture was then diluted with 56.7 g of toluene and was separated. To the aqueous layer was added dropwise 122.3 g of 20% by weight sodium hydroxide aqueous solution at a temperature of 20° C. or lower. The mixture was diluted with 113.4 g of toluene and was separated, and the toluene layer was fractionated. The aqueous layer was extracted with 75.6 g of toluene, and the toluene layer was fractionated. These toluene layers were added together, were concentrated under reduced pressure and thereby yielded 3.7 g of (S)-7-amino-5-benzyl-5-azaspiro[2.4]heptane.

$^1$H-NMR (CDCl$_3$) ppm: 0.25–0.35 (m, 1H, cyclopropyl), 0.47–0.58 (m, 2H, cyclopropyl), 0.63–0.70 (m, 1H, cyclopropyl), 2.34–2.41 (m, 2H, C$\underline{H}_2$), 2.58 (d, 1H, J=9.18, C$\underline{H}$), 2.97–3.04 (m, 2H, C$\underline{H}_2$), 3.54 (dd, 2H, J=13.0, 18.6, C$\underline{H}_2$), 7.09–7.31 (m, 5H, Ph)

While the present invention has been described with reference to what are presently considered to be the preferred embodiments, it is to be understood that the invention is not limited to the disclosed embodiments. On the contrary, the invention is intended to cover various modifications and equivalent arrangements included within the sprit and scope of the appended claims. The scope of the following claims is to be accorded the broadest interpretation so as to encompass all such modifications and equivalent structures and functions.

What is claimed is:

1. A process for the preparation of an optically active amine, the process comprising the steps of:

(A) reacting a ketone of following Formula (7) or (8):

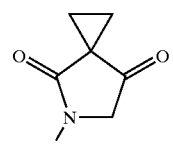

(7)

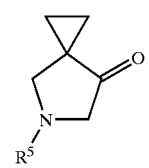

(8)

wherein $R^5$ is an unsubstituted or substituted aryl-lower group, with an optically active amine of following Formula (2):

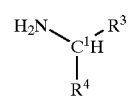

(2)

wherein $R^3$ is an unsubstituted or substituted aryl group; $R^4$ is an unsubstituted or substituted lower alkyl group; and $C^1$ is an asymmetric carbon atom, in the presence of an organic acid to thereby yield an optically active imine of following Formula (11) or (12):

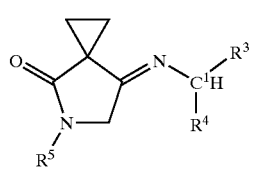

(11)

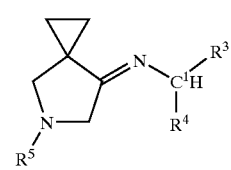

(12)

wherein $R^3$, $R^4$, $R^5$, and $C^1$ have the same meanings as defined above; and (B) hydrogenating the optically active imine of Formula (11) or (12) in the presence of a catalyst to thereby yield an optically active amine of following Formula (9) or (10):

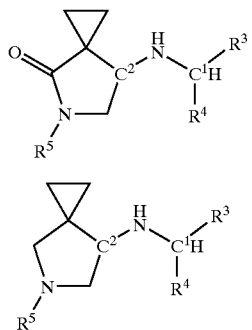

wherein $R^3$, $R^4$, $R^5$, and $C^1$ have the same meanings as defined above; and $C^2$ is an asymmetric carbon atom.

2. The process according to claim 1, wherein the organic acid in the step (A) is acetic acid.

3. The process according to claim 1, wherein $C^1$ is an asymmetric carbon atom with the R-configuration, and wherein $C^2$ is an asymmetric carbon atom with the S-configuration.

4. The process according to claim 1, wherein $C^1$ is an asymmetric carbon atom with the S-configuration, and wherein $C^2$ is an asymmetric carbon atom with the R-configuration.

5. The process according to claim 1, wherein $R^3$ is a phenyl group and $R^4$ is a methyl group in Formula (2), and wherein $R^5$ is a benzyl group in Formulae (7), (8), (9), (10), (11), and (12).

* * * * *